US00PP21664P3

(12) United States Plant Patent
Cain

(10) Patent No.: US PP21,664 P3
(45) Date of Patent: Jan. 25, 2011

(54) GRAPEVINE 'IFG 68-175'

(50) Latin Name: *Vitis vinifera*
Varietal Denomination: IFG 68-175

(75) Inventor: David Cain, Bakersfield, CA (US)

(73) Assignee: International Fruit Genetics, Bakersfield, CA (US)

( * ) Notice: Subject to any disclaimer, the term of this patent is extended or adjusted under 35 U.S.C. 154(b) by 0 days.

(21) Appl. No.: 12/455,739

(22) Filed: Jun. 5, 2009

(65) Prior Publication Data

US 2010/0313316 P1 Dec. 9, 2010

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annetta H Para
(74) *Attorney, Agent, or Firm*—Townsend and Townsend and Crew LLP

(57) ABSTRACT

This invention is a new and distinct grapevine variety denominated 'IFG 68-175'. 'IFG 68-175' is characterized by producing large bright red, crisp, uniform berries with high sugar content borne on medium size clusters. The fruit ripen and are commercially harvestable from late August to mid-September. Berries color fully even under adverse conditions and do not darken excessively throughout the harvestable period.

1 Drawing Sheet

Latin name of the genus and species of the plant claimed: *Vitis vinifera.*

Variety denomination: 'IFG 68-175'.

BACKGROUND OF THE INVENTION

The new and distinct grapevine described and claimed herein originated from a hand pollinated cross of the Redglobe variety (U.S. Plant Pat. No. 4,787 expired) and the Princess variety (non-patented) performed in May 2001. The seeds were subsequently germinated and the resulting plants were planted in the field in April 2002. The present variety of grapevine was selected as a single plant in August 2003 and was first asexually propagated by hardwood cuttings in December 2003. The resulting propagules were planted during April 2004 near Delano, Kern County, Calif. and were found to reproduce true-to-type through at least three generations of asexual reproduction. Further, the variety was asexually reproduced at a research facility near Delano, Kern County, Calif.

BRIEF SUMMARY OF THE INVENTION

The new grapevine 'IFG 68-175' is characterized by producing naturally large, round to oval red seedless berries which ripen in mid-season near the end of the Flame Seedless variety and before the Crimson variety. Berries have crisp texture, excellent eating quality and are able to develop bright red skin color more readily that existing commercial varieties. It does not require extensive leaf removal or ethrel applications to color properly. The desirable bright red skin color does not darken significantly as sugar levels increase.

To the inventor's knowledge, the known varieties to which the new grapevine variety is most similar are the Sheegene-6 variety (U.S. Plant Pat. No. 19,041), the Sheegene-1 and the 90-3618 variety (U.S. Plant Pat. No. 17,211). 'IFG 68-175' can be distinguished from the Sheegene-6 variety by ripening later (late August to early September as opposed to late July to early August for Sheegene-6), by having a more crisp flesh texture and somewhat smaller cluster size. 'IFG 68-175' has a V shaped petiolar sinus while Sheegene-6 has a U shaped petiolar sinus. The 'IFG 68-175' variety can be distinguished from the Sheegene-1 variety by ripening somewhat earlier (late August as opposed to mid September for Sheegene-1). 'IFG 68-175' has a more round berry shape than Sheegene-1 and it has a more firm, crisp texture. The 'IFG 68-175' variety can be distinguished from the '90-3618' variety by having a brighter, more desirable red color as opposed to a darker purple red color described for '90-3618'. 'IFG 68-175' has a V shaped petiolar sinus while '90-3618' has a U shaped petiolar sinus. Average berry weight of 'IFG 68-175' is somewhat smaller than '90-3618'. The new variety 'IFG 68-175' thus distinguishes itself from other grape varieties based on a unique combination of characteristics, which include naturally large crisp, very uniform berries with both high visual attractiveness and high eating quality combined with viticultural characteristics that reduce growing costs. 'IFG 68-175' can further be distinguished based on the characteristics described below.

BRIEF DESCRIPTION OF THE DRAWINGS

The accompanying photographic illustration in FIG. 1 illustrates in full color 'IFG 68-175'. The photograph was taken outdoors with indirect lighting. The colors are as nearly true as is reasonably possible in a color representation of this type.

DETAILED DESCRIPTION OF THE INVENTION

Figure 1:
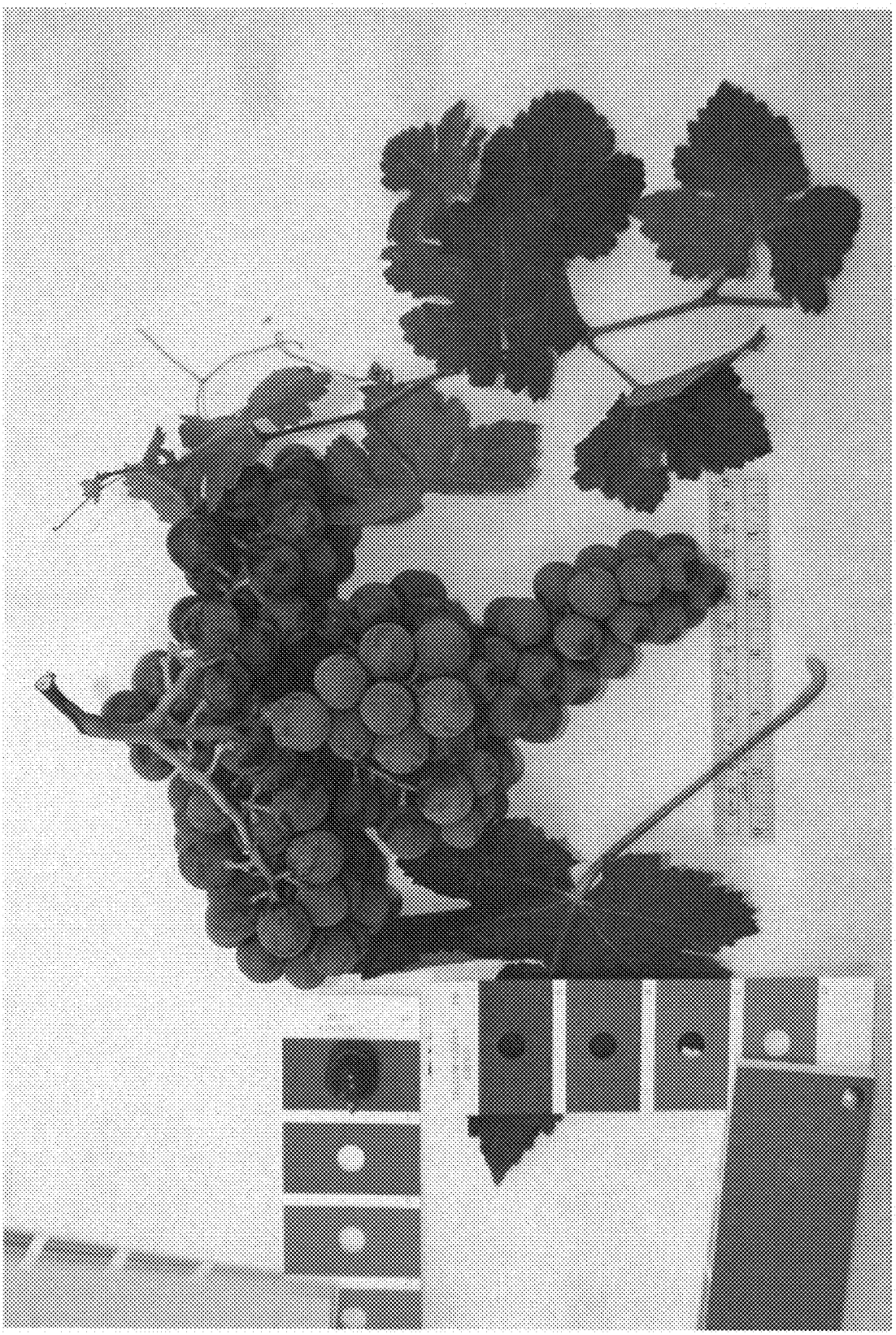

Throughout this specification, color names beginning with a small letter signify that the name of that color, as used in common speech, is aptly descriptive. Color names beginning with a capital letter designate values based upon The R.H.S. Colour Chart, published by The Royal Horitcultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The descriptive matter which follows pertains to 'IFG 68-175' plants grown in the vicinity of Delano, Kern County, Calif. during 2007-2008, and is believed to apply to plants of the variety grown elsewhere under similar soil and climate conditions:

Vine:

*General.*—Size — Medium. Vigor — Vigorous. Density of foliage — Medium. Productivity — Productive. Root stock — Own root. Training method — Typically spur pruned leaving two bud spurs.

*Trunk.*—Trunk diameter of 4-year-old vines at 30 cm above the soil line — 6.8 cm. Shape — Medium. Straps — Short-Split. Surface texture — Medium shaggy with short, loose straps. Inner bark color — 174A.

Shoots:

*Young shoot.*—Form of tip — Wide open. Distribution of anthocyanin coloration of tip — Absent. Intensity of anthocyanin coloration of tip — Absent. Density of prostrate hairs of tip — Sparse. Density of erect hairs on tip — Absent. Color — Yellow green 144A.

*Woody shoot* (*mature canes*).—Shape — Stocky. Internode length — Long; About 119.8 mm. Width at node — About 12.3 mm. Cross section — Circular. Surface — Smooth. Main color — Reddish brown 166C. Density of erect hairs on nodes — None or very sparse. Density of erect hairs on internodes — None or very sparse. Growth of axillary shoots — Medium; Approximately 11.9 cm.

*Flowering shoot.*—Vigor during flowering — Strong. Attitude during flowering on shoots not tied — Drooping. Color — dorsal side of internodes — Green with Red stripes. Color — ventral side of internodes Green 144A. Color — dorsal side of nodes — Green with Red stripes. Color — ventral side of nodes — Green with Red stripes. Density of prostrate hairs on nodes — None or sparse. Density of erect hairs on nodes — None. Density of prostrate hairs on internodes — None. Density of erect hairs on internode — None. Anthocyanin coloration of buds — Absent.

*Tendrils.*—Distribution on the shoot (at full flowering) — Discontinuous. Length of Tendril — Very long; About 33.5 cm. Thickness — Medium. Color — Yellow green N144A. Form — Trifurcated. Number of consecutive tendrils — 2.

Leaves:

*Young leaves.*—Color of upper surface of first four distal unfolded leaves — Green with bronze spots. Average intensity of anthocyanin coloration of six distal leaves prior to flowering — Medium. Density of prostrate hairs between veins (lower surface) — Absent. Density of prostrate hairs on veins(lower surface) — Sparse. Density of erect hairs between veins (lower surface) — Absent. Density of erect hairs on veins (lower surface) — Sparse.

*Mature leaves.*—Average length — About 11.8 cm. Width — About 14.0 cm. Mature leaf size — Large. Shape of blade — Cordate. Number of lobes — 5. Anthocyanin coloration of main veins on upper side of blade — Absent. Mature leaf profile — Flat. Blistering surface of blade upper surface — Weak. Leaf blade tip — In the plane of the leaf. Undulation of margin — Slight. Thickness. — Medium — Thin. Undulation of blade between main and lateral veins — Absent. Shape of teeth — Mixture of both sides straight and both sides convex. Length of teeth — Medium. Ratio length/width of teeth — Small. Shape of upper lateral sinuses — Closed. Depth of upper lateral sinuses — Shallow. Shape of base of upper leaf sinuses — V-shaped. Density of prostrate hairs between veins on lower surface of blade — Absent. Density of erect hairs between veins on lower surface of blade — Absent. Density of prostrate hairs on main veins on lower surface of blade — None or very sparse. Density of erect hairs on main veins on lower surface of blade — Sparse. Density of prostrate hairs on main veins on upper surface of blade — Sparse. Density of erect hairs on main veins on upper surface of blade — None. General shape petiole sinus — Closed — Lobes slightly overlapping. Shape of base of petiole sinus — V-shaped. Mature leaf tooth at petiole sinus — Absent.

*Upper surface.*—Color — 146B. Anthocyanin coloration of main veins — Absent. Surface appearance — Semi glossy. Blistering surface of blade — Weak.

*Lower surface.*—Color — 147A. Anthocyanin coloration of main veins (lower surface) — Absent. Glossiness — Weak. Surface texture — Rugose. Surface appearance — Semi-gloss.

*Petiole.*—Length — About 8.6 cm. Length of petiole compared to middle vein — Slightly shorter. Density of prostrate hairs on petiole — None to sparse. Density of erect hairs on petiole — None.

*Buds.*—Bud fruitfulness — Basal: Mostly fruitful. Position of first fruitful shoot on previous season cane — 1st to 2nd node. Time of bud burst — Late, Mar. 8, 2008.

Flowers:

*General.*—Flower sex — Hermaphrodite. Length of first inflorescence — Medium; 24.1 cm long by 15.8 cm wide. Position of first flowering and fruiting node — 4th node (current season growth). Number of inflorescences per flowering shoot — 1.1 to 2. Date of full bloom — May 10, 2007. Time of bloom — Mid-season as compared with similar varieties in the growing area of Delano, Calif.

Fruit:

*General.*—Ripening period — Mid — late season; Approximately Aug. 21, 2007. Use — Fresh market. Keeping quality — Excellent. Resistance to — insects: average typical of *Vitis vinifera* species; diseases: average typical of *Vitis vinifera* species. Shipping quality — good. Refractometer test — Solid-sugar: About 21.8 Brix. Brix/Acid — About 0.47. Titratable acidity — About 0.47. Juice pH — About 3.61.

*Cluster.*—Mature Cluster length (peduncle excluded)—About 22.2 cm. Mature Cluster width — About 15.0 cm. Mature Cluster weight — About 797 g. Bunch density — Dense requires thinning with gibberellic acid. Number of berries — About 128. Form — Conical.

*Peduncle.*—Length of peduncle — Medium; Approximately 7.2 cm. Lignification of peduncle — Strong.

*Berry.*—Uniformity of size — Uniform. Single berry weight — About 7.0 grams. Shape — Obtuse ovate. Seed — Contains small rudimentary seed traces, occasionally noticeable when eaten. Berry dimensions — longitudinal axis: About 2.5 cm, horizontal axis: About 2.1 cm. Skin color (without bloom) — Red group 46A. Berry firmness — Firm and crisp. Particular flavor — Neutral. Bloom (cuticular wax) — Strong. Berry separation from pedicel — Difficult.

*Skin.*—Thickness — Medium. Texture — Medium. Reticulation — Absent. Tenacity — Tenacious to flesh.

The variety has no particular disease or insect resistance and is similar in susceptibility to other commonly grown *Vitis vinifera* varieties. It requires similar protective measures as required for other common *vinifera* varieties to be grown commercially.

What is claimed is:

1. A new and distinct variety of grapevine plant having the characteristics substantially as described and illustrated herein.

* * * * *